United States Patent
Kokubun et al.

(10) Patent No.: US 7,620,443 B2
(45) Date of Patent: Nov. 17, 2009

(54) X-RAY CT IMAGING METHOD AND X-RAY CT DEVICE

(75) Inventors: Hiroto Kokubun, Chiba (JP); Osamu Miyazaki, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 418 days.

(21) Appl. No.: 10/501,121

(22) PCT Filed: Jan. 9, 2003

(86) PCT No.: PCT/JP03/00090

§ 371 (c)(1),
(2), (4) Date: Feb. 28, 2005

(87) PCT Pub. No.: WO03/059167

PCT Pub. Date: Jul. 24, 2003

(65) Prior Publication Data

US 2005/0129176 A1    Jun. 16, 2005

(30) Foreign Application Priority Data

Jan. 10, 2002   (JP) .............................. 2002-003321

(51) Int. Cl.
*A61B 5/05* (2006.01)
*G06K 9/00* (2006.01)
*H01J 35/00* (2006.01)

(52) U.S. Cl. ........................ 600/428; 378/125; 382/131; 382/132; 600/425

(58) Field of Classification Search ................. 600/411, 600/425–429, 413; 382/132, 131; 378/23
See application file for complete search history.

(56) References Cited

U.S. PATENT DOCUMENTS

| | | | | |
|---|---|---|---|---|
| 4,969,110 A | * | 11/1990 | Little et al. | 382/131 |
| 5,751,782 A | * | 5/1998 | Yoshitome | 378/98.5 |
| 5,832,051 A | * | 11/1998 | Lutz | 378/8 |
| 5,987,091 A | * | 11/1999 | Miyazaki et al. | 378/15 |
| 5,991,356 A | * | 11/1999 | Horiuchi et al. | 378/8 |
| 6,002,738 A | * | 12/1999 | Cabral et al. | 378/4 |
| 6,041,097 A | * | 3/2000 | Roos et al. | 378/62 |
| 6,088,611 A | * | 7/2000 | Lauterbur et al. | 600/407 |
| 6,233,478 B1 | * | 5/2001 | Liu | 600/428 |
| 6,243,437 B1 | * | 6/2001 | Hu et al. | 378/8 |
| 6,266,553 B1 | * | 7/2001 | Fluhrer et al. | 600/428 |
| 6,381,487 B1 | * | 4/2002 | Flohr et al. | 600/425 |

(Continued)

FOREIGN PATENT DOCUMENTS

JP        2000189412        7/2000

(Continued)

*Primary Examiner*—Eric F Winakur
*Assistant Examiner*—Helene Bor
(74) *Attorney, Agent, or Firm*—Cooper & Dunham, LLP

(57) ABSTRACT

An X-ray CT apparatus can be configured such that an amount of artifacts of a tomographic image of a heart is reduced. For example, the X-ray CT apparatus can include detecting means for detecting a static cardiac time phase with a small amount of motion artifacts in a predetermined portion of the subject based on heartbeat information acquired in association with the projection data, and image reconstructing means for generating the tomographic image by reconstructing projection data corresponding to the static cardiac time phase detected by the detecting means.

19 Claims, 5 Drawing Sheets

U.S. PATENT DOCUMENTS

| | | |
|---|---|---|
| 6,421,552 B1 * | 7/2002 | Hsieh .......................... 600/425 |
| 6,697,508 B2 * | 2/2004 | Nelson ....................... 382/131 |
| 6,980,682 B1 * | 12/2005 | Avinash et al. .............. 382/131 |
| 2001/0034482 A1 * | 10/2001 | Webber et al. .............. 600/407 |
| 2006/0120586 A1 * | 6/2006 | Iatrou et al. ................. 382/131 |

FOREIGN PATENT DOCUMENTS

JP     2001137232     5/2001

* cited by examiner

X-RAY CT IMAGING METHOD AND X-RAY CT DEVICE

TECHNICAL FIELD

The present invention relates to an X-ray CT (computed tomography) imaging method and apparatus, and more particularly, to an X-ray CT imaging method and apparatus that can acquire an image in the same time phase of a cyclic motion of an imaging subject such as a heart and the like.

BACKGROUND ART

In general, in a CT examination of a heart, motion artifacts appear in a tomographic image by the effect of a heartbeat, which results in an unpreferable image in diagnosis. To reduce the motion artifacts, there has been proposed to reduce the effect of the heartbeat by increasing a scan speed as compared with one heartbeat cycle. However, a beat rate of a heart of a human body is different depending on persons and on a physical condition and a mental condition of a person at the time even if they are the conditions of the same person.

Accordingly, heretofore, there is proposed a method of executing imaging by adding a heartbeat waveform to a scan data in asynchronism with a heartbeat cycle and rearranging an image by combining projection data having the same heartbeat time phase (hereinafter, referred to as (cardiac time phase) in Japanese Unexamined Patent Application Publication No. JP2001-137232A. In this publication, a heartbeat cycle of a subject is measured, projection data is acquired by scanning the heart of a subject at an angular speed that is in asynchronism with the measured heartbeat cycle, and a tomographic image of the heart of the subject is generated from of projection image segments that are discrete in time. The generated image corresponds to a selected portion of the heartbeat cycle, for example, to a relatively static portion thereof.

That is, the publication discloses to reduce motion artifacts due to the effect of a heartbeat by acquiring a tomographic image of a heart by rearranging the image of projection data imaged in a cardiac time phase, in which the motion of the heart is minimized (hereinafter, referred to as static cardiac time phase), using heartbeat information. Here, the cardiac time phase is a concept of a heartbeat cycle that is divided into a plurality of sections. The cardiac time phase can be expressed by equally dividing an interval of an R wave, which appears periodically in a heartbeat waveform, into "n" time sections (n is an integer) and referring the equally divided time sections as cardiac time phases so that the respective cardiac time phases can be sequentially expressed from the R wave acting as a reference. Otherwise, the cardiac time phase can be also expressed by a percentage by setting an R wave cycle to 100% and expressing the cardiac time phase by a position on a time axis from the R waveform acting as the reference. That is, when the static cardiac time phase is expressed, it can, be expressed by a relative position (%) of it from the R wave acting as the reference with the R wave cycle expressed by 100% as shown in FIG. 2.

However, a cardiac time phase that is less affected by a heartbeat is different depending on a portion of a heart or on a portion in the vicinity of the heart. Accordingly, there is a possibility that motion artifacts are generated unless an appropriate static cardiac time phase is determined according to an observing portion and unless an image is rearranged using projection data corresponding to the static cardiac time phase. Further, as described above, the static cardiac time phase varies depending on a patient to be imaged and on a health condition of the patient. Accordingly, a tomographic image of a heart with a small amount of motion artifacts may not be acquired in a static cardiac time phase determined by an apparatus. In this case, it is contemplated to generate a plurality of tomographic images in a different cardiac time phase at the same measuring position and to select a tomographic image with a small amount of motion artifacts from the plurality of tomographic images. However, it takes a long time to generate the plurality of tomographic images, and it is time-consuming for an operator to select an image with a small amount of motion artifacts from the plurality of tomographic images.

DISCLOSURE OF INVENTION

An object of the present invention is to provide an X-ray CT imaging method and an X-ray CT apparatus that can acquire a tomographic image of a heart with a small amount of motion artifacts due to a heartbeat at a position to which attention is paid in a short time.

An X-ray CT imaging method of the present invention for generating a tomographic image by reconstructing projection data acquired by scanning a predetermined slice of a subject is characterized in that a static cardiac time phase with a small amount of motion artifacts is detected in a predetermined portion of the subject based on heartbeat information acquired in association with the projection data, and the tomographic image is generated by reconstructing projection data corresponding to the detected static cardiac time phase.

Here, correlation data between the heartbeat information and the static cardiac time phase is previously prepared to the subject, and the static cardiac time phase corresponding to the acquired heartbeat information can be detected based on the correlation data.

Further, a plurality of sample tomographic images having a different cardiac time phase can be generated based on the projection data and the heartbeat information, a sample tomographic image with a small amount of motion artifacts can be selected from the plurality of sample tomographic images, and a cardiac time phase corresponding to the selected sample tomographic image can be detected as a static cardiac time phase. In this case, it is preferable to set an image size of the sample tomographic image smaller than that the tomographic image. Further, it is also possible to previously prepare correlation data between the heartbeat information and the static cardiac time phase to the subject and to generate the plurality of sample images in a predetermined cardiac time phase range determined based on the correlation data.

An X-ray CT apparatus of the present invention for generating a tomographic image by reconstructing projection data acquired by scanning a predetermined slice of a subject is characterized by including a detecting means for detecting a static cardiac time phase with a small amount of motion artifacts in a predetermined portion of the subject based on heartbeat information acquired in association with the projection data, and an image reconstructing means for generating the tomographic image by reconstructing projection data corresponding to the static cardiac time phase detected by the detecting means.

According to the present invention, since the static cardiac time phase is detected based on the heartbeat information, it is possible to more accurately set the static cardiac time phase of an observing portion and to reduce an amount of motion artifacts.

Further, the detecting means may detect the static cardiac time phase based on correlation data between the heartbeat information and the static cardiac time phase that are determined previously to each subject. In this case, to cope with that each portion a body has a different static cardiac time phase, the correlation data is prepared to each of the different portions of the body, and an input means is provided to set a predetermined portion to the detecting means. In this case, the names of the portions whose the correlation data are prepared may be displayed on the display device so that an operator can selects the names. Further, since it is known that the static cardiac time phase varies depending on a heat rate, the correlation data can be arranged so as to include at least a correlation between the heartbeat rate and the static cardiac time phase.

Incidentally, projection data corresponding to a detected static cardiac time phase may be acquired in a one heartbeat cycle. However, the projection data may be acquired over a plurality of heartbeat cycles, the projection data may be synthesized in the static cardiac time phase of each cycle, and the tomographic image may be reconstructed based on the synthesized projection data. That is, the X-ray CT apparatus may include a memory means for storing the projection data acquired over the plurality of heartbeat cycles and the projection data synthesizing means for reading the projection data corresponding to the static cardiac time phase detected by the detecting means and synthesizing the projection data, and the image reconstructing means may reconstruct the projection data synthesized by the projection data synthesizing means.

In contrast, the detecting means may include a sample tomographic image rearranging means for generating a plurality of sample tomographic images having a different cardiac time phase based on the projection data and the heartbeat information and a selecting means for selecting a sample tomographic image with a small amount of motion artifacts from the plurality of sample tomographic image, and the image reconstructing means generates the tomographic image by reconstructing projection data corresponding to the cardiac time phase of the sample tomographic image selected by the selecting means. According to the above arrangement, since a most appropriate cardiac time phase can be selected from the cardiac time phases corresponding to the respective sample tomographic images, the amount of motion artifacts can be reduced.

Incidentally, to select the cardiac time phase with the small amount of motion artifacts, it is sufficient for the sample tomographic image to have an image size that includes at least an observing portion, that is, a so-called region of interest. Accordingly, the size of the sample tomographic image may be set smaller than that of the tomographic image. According to the above arrangement, an arithmetic operation time necessary to reconstruct the sample tomographic image can be reduced and a sample tomographic image generating speed is increased, thereby a tomographic image with the small amount of motion artifacts of the portion of interest can be acquired in a short time.

In this case, the selecting means may be arranged such that it calculates an integrated value of a CT value of each of the plurality of sample tomographic images having a different cardiac time phase in a selected region at the arbitrary imaging position and selects a sample tomographic image with a smallest fluctuation of the integrated value of the CT value, it selects a sample tomographic image in the cardiac time phase having a largest correlation, or determines a difference between integrated values of CT values of tomographic images having adjacent cardiac time phases and selects a sample tomographic image having a smallest difference. According to the above arrangements, the static cardiac time phase with the small amount of motion artifacts can be acquired at an arbitrary position.

Further, since the tomographic image is reconstructed using the projection data acquired over a plurality of heartbeat cycle also in this case, the X-ray CT apparatus may include a memory means for storing the projection data acquired over a plurality of heartbeat cycles and a projection data synthesizing means for reading the projection data corresponding to the cardiac time phase of the sample tomographic image selected by the selecting means and synthesizing the projection data, and the image reconstructing means may reconstruct the projection data synthesized by the projection data synthesizing means.

Further, the sample tomographic image may be generated at uniform or equal intervals over the heartbeat cycle. However, a range of the cardiac time phase, which is previously predicted to include the static cardiac time phase, may be detected and the sample tomographic image may be generated only in the range or at dense time intervals in the range. Thus, the sample image generating means may generate a plurality of sample tomographic images in the predetermined cardiac time phase range determined based on the correlation data between the heartbeat information and the static cardiac time phase that are determined previously. According to the above arrangement, the static cardiac time phase can be detected rapidly and the tomographic image with the small amount of motion artifacts can be acquired in a short time.

The correlation data may be prepared to different portions of the subject also in this case, and the detecting means may be provided with an input means for setting a predetermined portion. Further, the correlation data may include at least a correlation between the heartbeat rate and the static cardiac time phase.

BEST MODE FOR CARRYING OUT THE INVENTION

An Embodiment of the present invention will be described below based on the figures.

Figure 1:
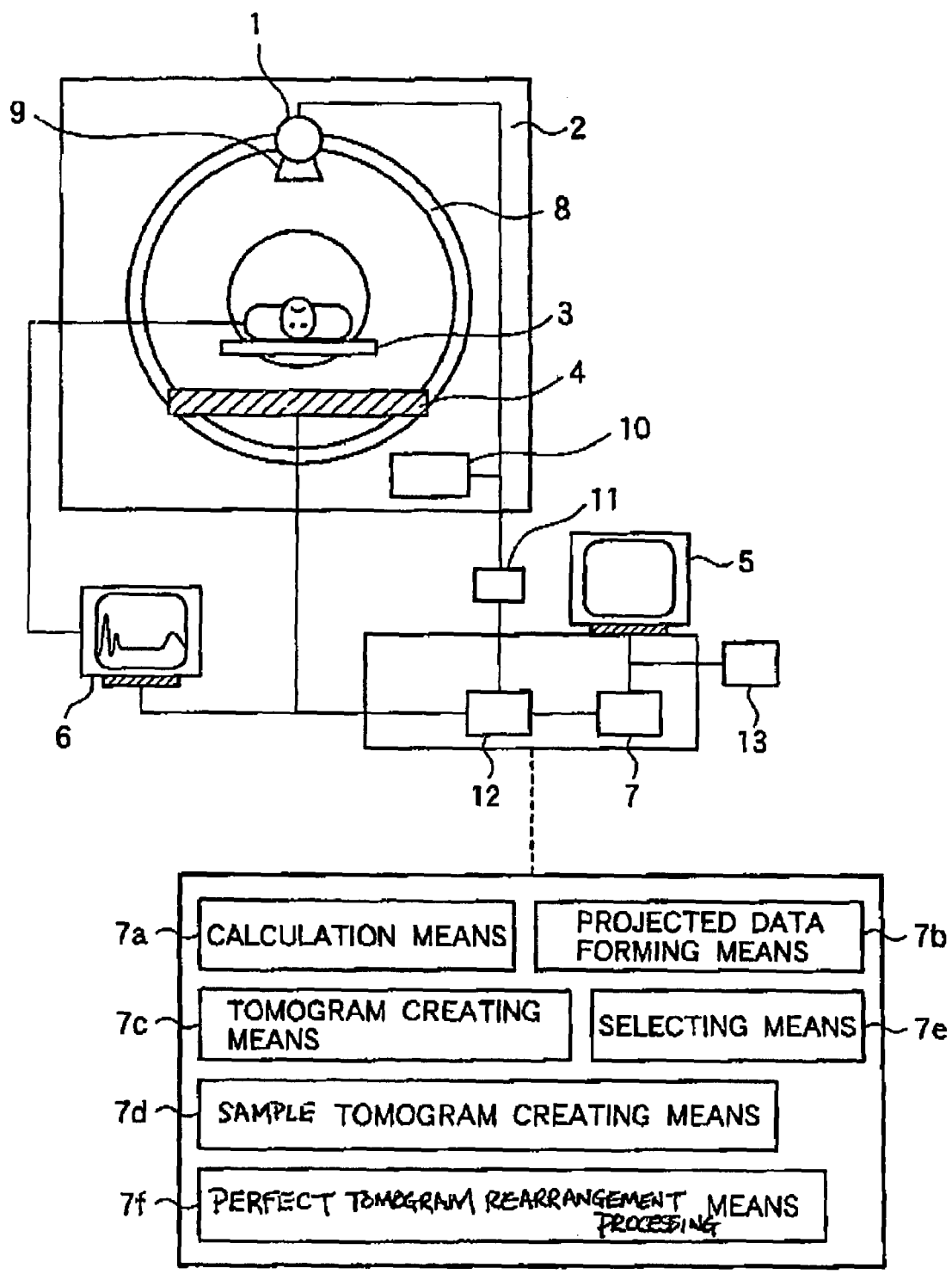
FIG. 1 is a block arrangement view showing an X-ray CT apparatus according to an embodiment of the present invention.
Figure 2:
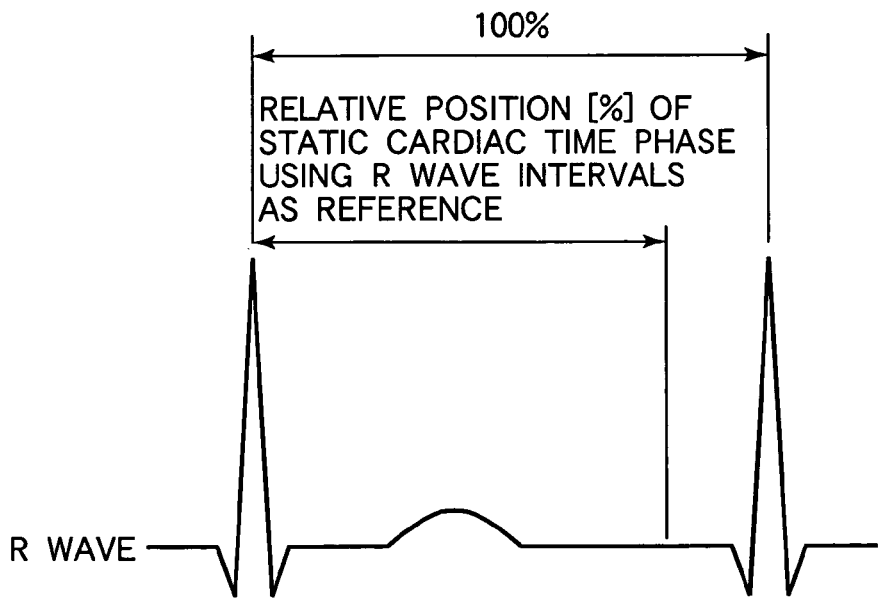
FIG. 2 is a characteristic view showing heartbeat information acquired from an electrocardiograph.

FIG. 1 is a block arrangement view showing a schematic arrangement of an X-ray CT apparatus according to an embodiment of the present invention.

The X-ray CT apparatus includes a scanner gantry unit 2 for irradiating and detecting X-rays, an image processing apparatus 7 for generating projection data from measurement data detected by the scanner gantry device 2 and processing the projection data to a CT image signal, and a display device 5 for outputting a CT image. The scanner gantry unit 2 includes a rotary disc 8, which is driven in rotation by a rotary drive device 10 controlled by a measurement control device 11, an X-ray tube 1 mounted on the rotary disc 8, a collimator 9 attached to the X-ray tube 1 for controlling a direction of X-ray flux, and an X-ray detector 4 mounted on the rotary disc 8. Further, an intensity of the X-rays generated from the X-ray tube 1 is controlled by the measurement control device 11 which is operated by a computer 12 having an input device 13. In contrast, the image processing apparatus 7 is connected to an electrocardiograph 6 for acquiring a heartbeat waveform of a subject.

The image processing apparatus 7 includes various functions of a calculation means 7a, a projection data forming means 7b, a tomogram creating means 7c, a sample tomogram creating means 7d, a selecting means 7e, a perfect tomogram rearrangement processing means 7f, and the like. The calculation means 7a is a detecting means for calculating a heartbeat rate of the subject from the intervals of an R wave at time at which an arbitrary position or slice is imaged based on the heartbeat information of the subject acquired in imaging, calculating a static cardiac time phase with a small amount of motion artifacts at an arbitrary body portion on the slice from the heartbeat rate, and detecting a static cardiac time phase. The projection data forming means 7b forms or synthesizes projection data that is acquired by combining projection data, which corresponds to the static cardiac time phase calculated by the calculation means 7a as well as is acquired over a plurality of heartbeat cycles in a projection angle range necessary to an image rearrangement arithmetic operation. The tomogram creating means 7c creates or generates a tomographic image at an arbitrary imaging position from the projection data acquired by the projection data forming means 7b by the image reconstitution. The sample tomographic image creation means 7d creates a plurality of tomographic images, in other words, sample tomographic images at the above imaging position in a different cardiac time phase on the rearranged image that has been subjected to the rearrangement processing at the above arbitrary imaging position. The selecting means 7e selects a tomographic image in a cardiac time phase with a smallest amount of motion artifacts from the plurality of tomographic images created by the sample tomogram creating means 7d. The perfect tomogram rearrangement processing means 7f creates a perfect tomographic image by subjecting the tomographic image selected by the selecting means 7e to perfect tomographid image rearrangement processing.

When X-rays are irradiated to a subject lying on a patient table 3 from the X-ray tube 1 as illustrated, the X-rays are provided with directivity by the collimator 9 and detected by the X-ray detector 4. At the time, the X-rays are detected using the X-ray detector 4 while changing a direction in which the X-rays are irradiated by rotating the rotary disc 8 around the subject. Measurement data detected as described above is transferred to the image processing apparatus 7. The image processing apparatus 7 forms projection data with a small amount of motion artifacts from the heartbeat information of the subject measured by the electrocardiograph 6 and imaging conditions acquired from the measurement control device 11, reconstructs the projection data to a CT image, and outputs the CT image to the display device 5.

Figure 3:
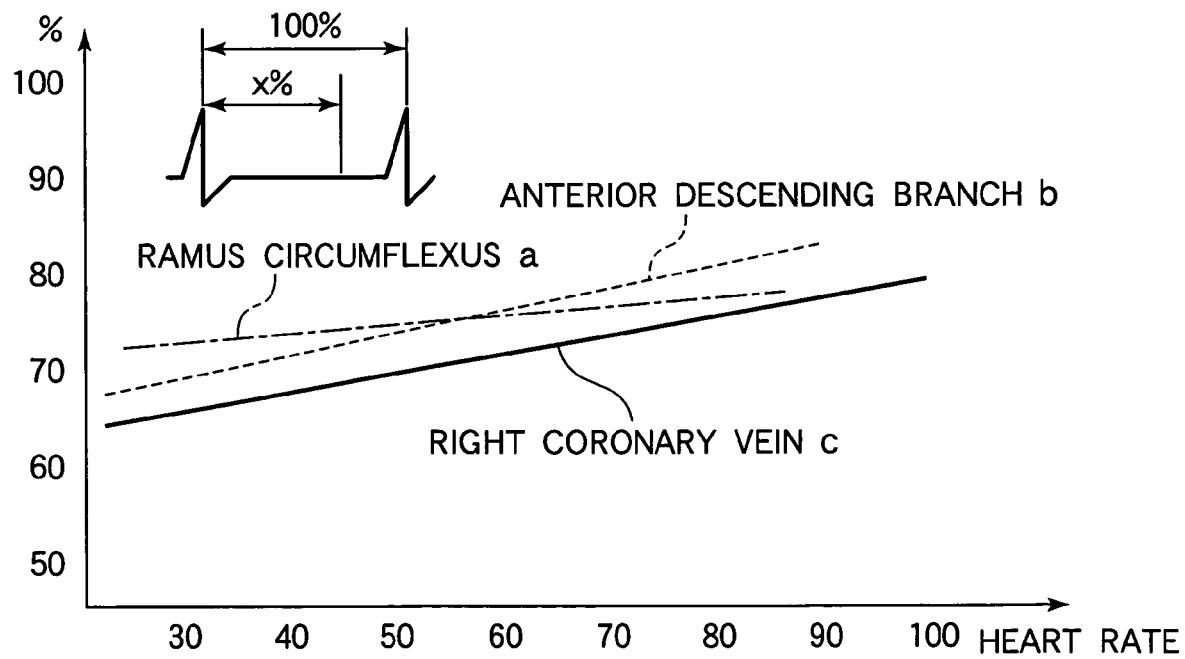
FIG. 3 is a characteristic view of a static cardiac time phase showing a relation between a static cardiac time phase and a heartbeat rate.

It is known that the static cardiac time phase is different depending on a portion of a heart and a portion of the periphery of the heart. Further, it is also known that the static cardiac time phase is affected by a heartbeat rate of a subject, and there is a relation as shown in FIG. 3. FIG. 3 shows a characteristic view of a static cardiac time phase cited from a general lecture No. 293 "Initial Experience of Heart CT by Cardiac-Synchronized Rearrangement Method Using Multi-Sliced CT" in Academic Symposium of 57th General Assembly of Japanese Society of Radiological Technology. In FIG. 3, a lateral axis shows a heartbeat rate of a subject, and a vertical axis shows a relative position between adjacent R waves by percentage. As shown in FIG. 3, respective portions such as a ramus circumflexus a, an anterior descending branch b, a right coronary artery c, and the like have such a tendency that an increase in a heartbeat rate increases a percentage of a static cardiac time phase. Further, it is found that the static cardiac time phase has a different increasing rate in respective portions. Further, the static cardiac time phase of FIG. 3 absolutely shows a tendency of an ordinary patient, and it varies depending on an individual difference of a patient as an imaging subject and a health condition of the patient.

When the heartbeat rate of the subject, which is measured by the electrocardiograph 6 in imaging, is found from the tendency shown in FIG. 3, a static cardiac time phase of a portion of a heart or a portion in the vicinity of the heart, to which the operator pays attention, can be determined, and a tomographic image with a smallest amount of motion artifacts can be acquired at the portion to which the operator pays attention by reconstructing projection data imaged in the static cardiac time phase.

Figure 4:
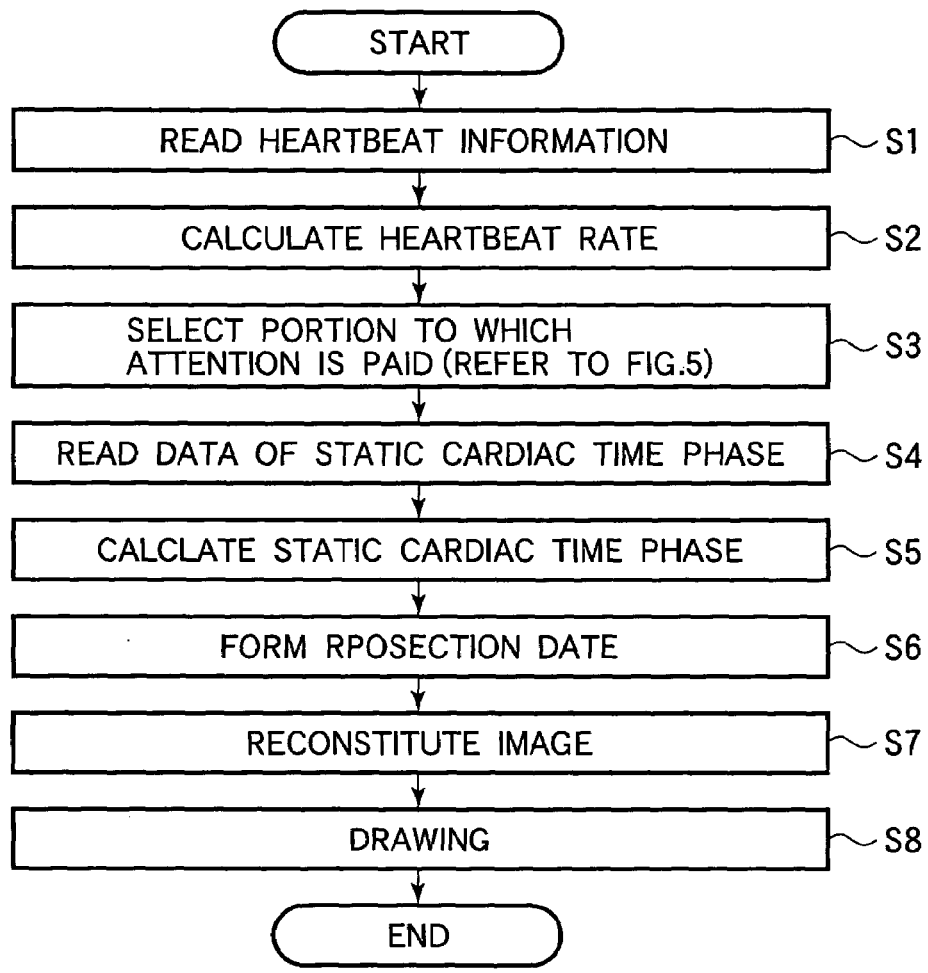
FIG. 4 is a flowchart showing processing for acquiring a tomographic image by the X-ray CT apparatus shown in FIG. 1.

FIG. 4 is a flowchart showing operation steps until a tomographic image with a small amount of motion artifacts is acquired by the X-ray CT apparatus described above.

First, at step S1, heartbeat information measured by the electrocardiograph 6 is read by the image processing apparatus 7. The calculation means 7a of the image processing apparatus 7 calculates a heartbeat rate of the subject in imaging from the thus read heartbeat information at step S2. Next, the operator designates a portion to which attention is paid through the input device 13 at step S3. The image processing apparatus 7 previously determines a relation between a heartbeat rate and a static cardiac time phase as shown in FIG. 3 of respective portions of a heart, i.e. a right coronary artery, a left coronary artery, a ramus circumflexus, and the like and respective portions in the vicinity of the heart, i.e. a lung artery, a lung vein, a lung field, and the like and stores the relation as data (hereinafter, referred to as static cardiac time phase data) and reads the heartbeat rate of the patient calculated at step S2 and data of a static cardiac time phase of an attention-paid-portion stored to the image processing apparatus 7 at step S4, and the calculation means 7a calculates a static cardiac time phase of the attention-paid-portion from them at step S5. At this time, the portion to which attention is paid is designated by displaying the name of data of the static cardiac time phase stored in the image processing apparatus 7 on a user interface 5a of the display device 5 and selecting designated portions 16a to 16n (including right and left coronary portions 16a and 16b, anterior descending branch portion 16c, ramus circumflexus portion 16d, etc.) using the input device 13, thereby the operator can smoothly select the portion to which attention is paid.

Next, at step S6, the projection data forming means 7b of the image processing apparatus 7 forms projection data within a projection angle range, which is necessary to reconstruct an image at an arbitrary sliced position, which was imaged in a static cardiac time phase, based on the heartbeat information. In this case, a method of collecting projection data having the same cardiac time phase from different scan data to enhance time resolution. The thus formed projection data is subjected to image reconstitution by the tomogram creating means 7c at step S7 and drawn on the display device 5 at step S8. These procedures permit a tomographic image with a smallest amount of motion artifacts to be acquired even at the portion to which the operator pays attention.

Figure 6:
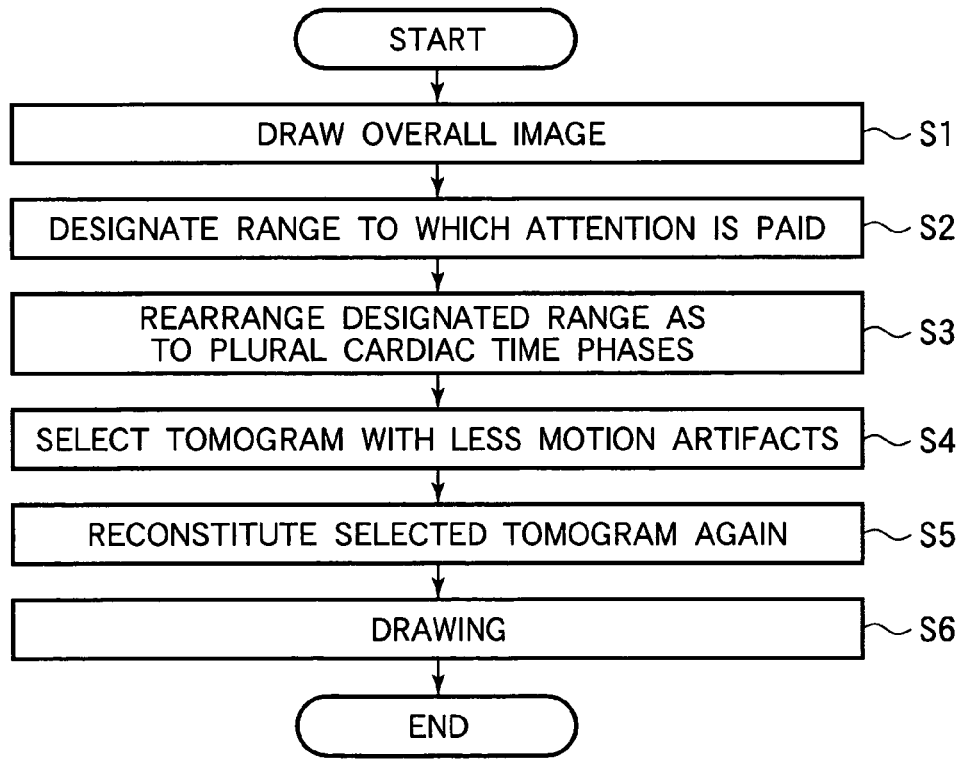
FIG. 6 is a flowchart showing other processing for acquiring a tomographic image by the X-ray CT apparatus shown in FIG. 1.

Since the static cardiac time phase varies depending on an observing patient and a health condition of the patient, motion artifacts may be generated even by the method shown in FIG. 4. A method of permitting a tomographic image with a small amount of motion artifacts to be acquired at an arbitrary sliced position even in the above case will be explained with reference to a flowchart shown in FIG. 6.

Figure 9:
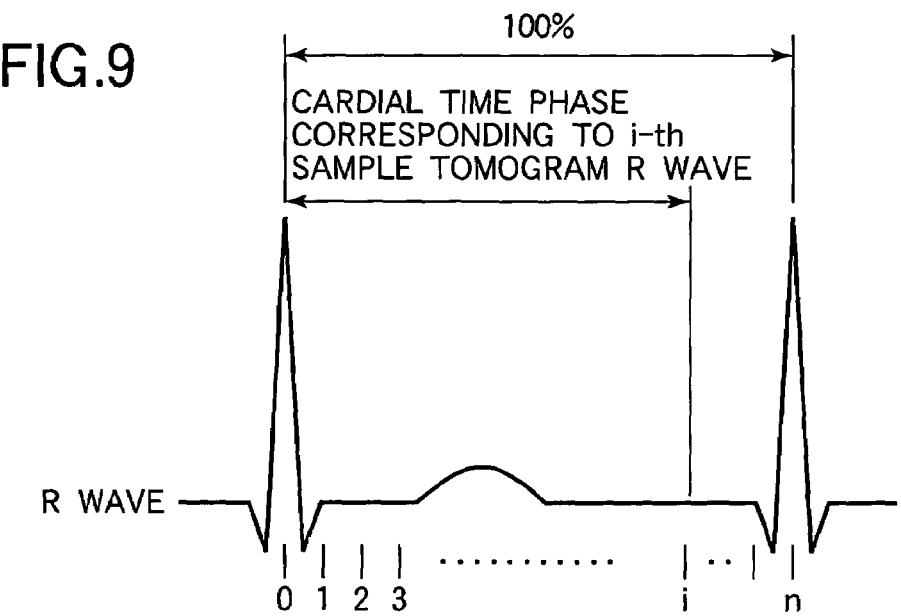
FIG. 9 is a view showing n types of cardiac time phases in which a plurality of tomographic images are generated.
Figure 5:
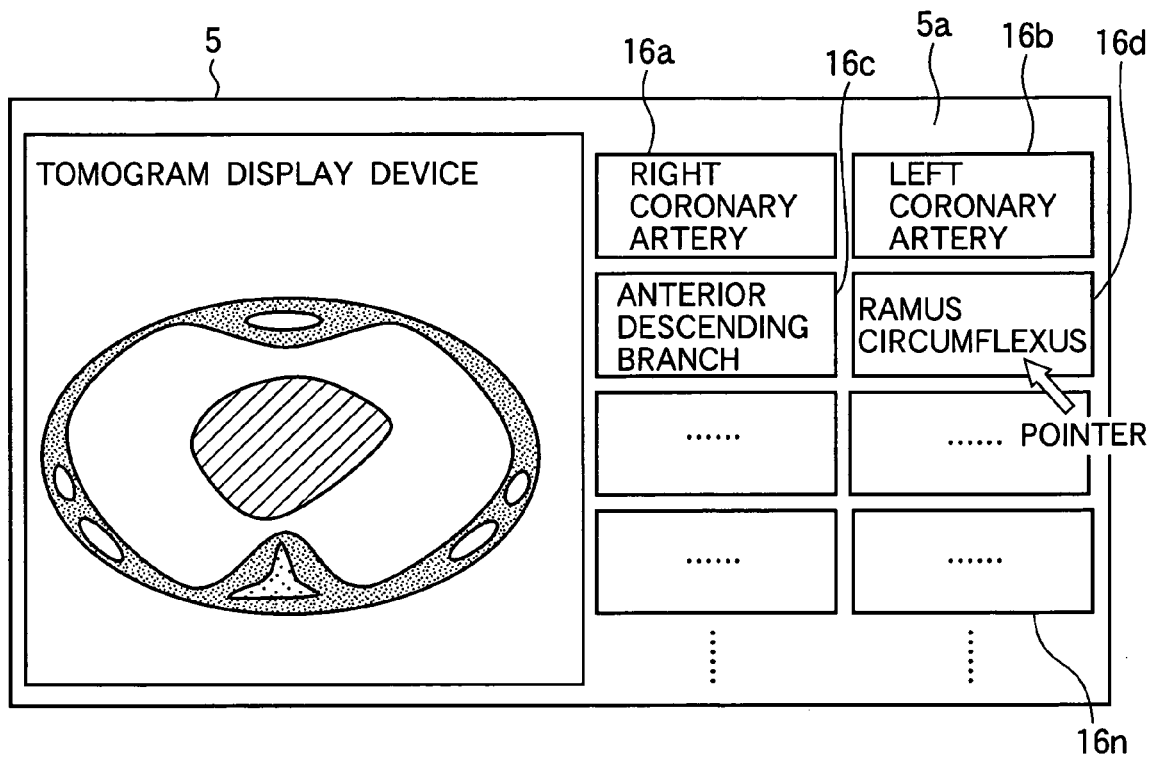
FIG. 5 is a front elevational view of a display device in the X-ray CT apparatus shown in FIG. 1.
Figure 7:
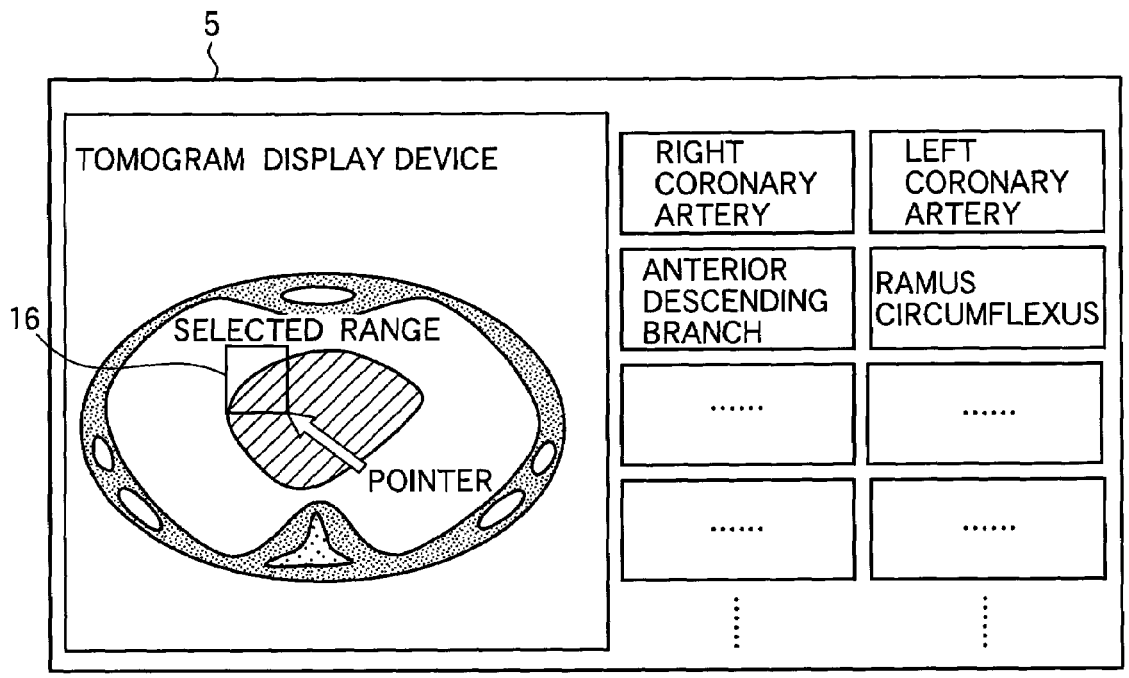
FIG. 7 is a front elevational view of the display device when the processing shown in FIG. 6 is executed.
Figure 8:
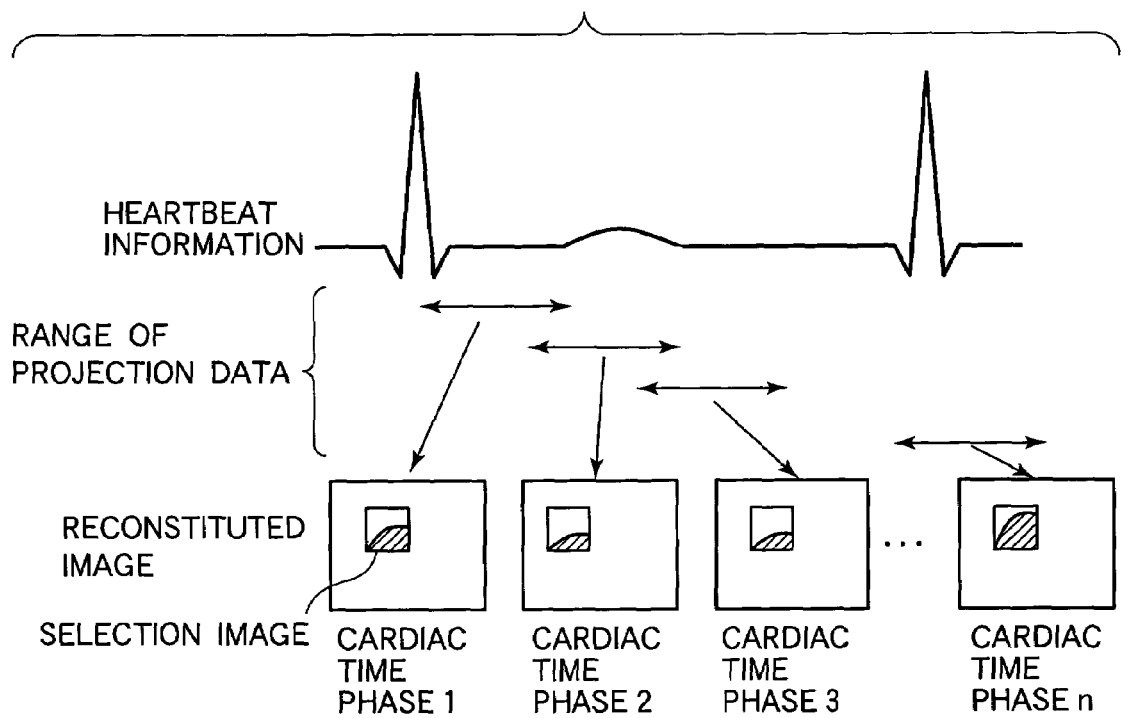
FIG. 8 is a process view explaining the processing shown in FIG. 6 in detail.

First, at step S1, a tomographic image at an arbitrary sliced position is displayed on the display device 5. Next, at step S2, the operator designates a range of an attention-paid-portion 16 using the input device 13 as shown in FIG. 7. Although it is preferable that the range be as small as possible to reduce a load on an arithmetic operation and to shorten a time necessary to generate sample tomographic images, it is preferable to set the range such that a portion, which is observed over at least one heartbeat cycle, is not located outside of the range by a body movement due to heat beats. Next, at step S3, the sample tomogram creating means 7d of the image processing apparatus 7 creates projection data in various cardiac time phases at the arbitrary sliced position as shown in FIG. 8 and subjects the respective projection data to the image reconstitution processing only in the range of the tomographic image designated at the previous step, on the tomographic image. In FIG. 8, projection data are generated in n kinds of cardiac time phases, and the respective projection data are subjected to the image reconstitution only in the selected range, thereby sample tomographic images are acquired in the n kinds of the cardiac time phases. FIG. 9 is a view showing a relation between a heartbeat waveform and n (n is an integer) types of cardiac time phases. As shown in FIG. 9, each of the n types of the cardiac time phases is a cardiac time phase appearing at every intervals when one heartbeat cycle is equally divided into n sections. Since the image reconstitution processing is executed only in the selected range, an arithmetic operation time is reduced as compared with a case that an entire image region is subjected to the image reconstitution processing. When, for example, a region whose range is designated, i.e. a size of a sample image is, for example, 64×64 pixels with respect to a tomographic image having, for example, 512×512 pixels, the arithmetic operation time is reduced 1/64.

Next, at step S4, the selecting means 7e selects a reconstructed image in a cardiac time phase with a smallest amount of motion artifacts from a plurality of reconstructed tomographic images having a different cardiac time phase. It is contemplated to employ the following methods as the selecting means 7e. To select a reconstructed image in a cardiac time phase with a small amount of motion artifacts, an integrated value of a CT value of each of the respective reconstructed images is determined in a region of interest (ROI) within the designated range. The resultant integrated values vary in every cardiac time phases, and a larger amount of shift of the attention-paid-portion results in a larger amount of variation of the integrated values. In other words, a reconstructed image in a cardiac time phase with a small amount of variation of the integrated value is a reconstructed image having a cardiac time phase with a smallest amount of motion artifacts in a portion within the range selected by the operator. A reconstructed image in a cardiac time phase with a smallest amount of motion artifacts is selected is selected using the method described above.

Otherwise, to select a reconstructed image in a cardiac time phase with a small amount of motion artifacts, the selecting means 7e determines a correlation between cardiac time phases forward and backward of each of the reconstructed images. A resultant correlation acquired to each image is varied by a cardiac time phase, and a larger amount of shift of the attention-paid-portion more reduces the correlation. That is, a reconstructed image in a cardiac time phase with a largest correlation is a reconstructed image having a cardiac time phase with a smallest amount of motion artifacts in a portion within the range selected by the operator.

Otherwise, to select a reconstructed image in a cardiac time phase with a small amount of motion artifacts, the selecting means 7e determines a difference between CT values of reconstructed images in forward and backward cardiac time phases in the respective reconstructed images. The difference between the respective images varies in every cardiac time phases, and a larger amount of shift of the attention-paid-portion results in a larger difference. That is, a reconstructed image in a cardiac time phase with a smallest difference is a reconstructed image having a cardiac time phase with a smallest amount of motion artifacts in a portion within the range selected by the operator.

The reconstructed image in the cardiac time phase with the smallest amount of motion artifact is selected using the selecting means 7e described above. Since the selected tomographic image is subjected to the image reconstitution only in the range designated by the operator, the image reconstitution is executed using the perfect tomogram image rearrangement processing means 7f of the image processing apparatus 7 at step S5, and a resultant perfect tomographic image is drawn on the display device 5. As described above, even if the static cardiac time phase varies, a tomographic image with a small amount of motion artifacts can be acquired at an arbitrary sliced position.

It should be noted that although the embodiment described above refer only to a two-dimensional tomographic image at an arbitrary sliced position, it is apparent that a three-dimensional image with a small amount of motion artifacts can be acquired in an attention-paid-portion by repeatedly executing similar processing at a plurality of sliced positions and using a plurality of resultant tomographic images.

As described above, according to the X-ray CT apparatus of the present invention, a static cardiac time phase with a small amount of motion artifacts can be acquired in any arbitrary portion of a body from a heartbeat rate, and moreover the static cardiac time phase is acquired in consideration of respective body portions. Accordingly, a tomographic image of a heart with a small amount of motion artifacts due to a heartbeat can be acquired in an attention-paid-portion in a short time.

The invention claimed is:

1. An X-ray CT apparatus for generating a tomographic image by reconstructing projection data acquired by scanning a predetermined slice of a subject, said X-ray CT apparatus comprising
   detecting means configured to detect a static cardiac time phase with a small amount of motion artifacts in a predetermined portion in a heart, vicinity thereof or tissues moving along therewith, of the subject based on heartbeat information acquired in association with the projection data, and
   image reconstructing means configured to generate the tomographic image by reconstructing projection data corresponding to the static cardiac time phase detected by the detecting means,
   wherein the detecting means determines the static cardiac time phase of the predetermined portion based on correlation data between the heartbeat information and the static cardiac time phase of each of a plurality of different portions of the subject, that are previously determined.

2. An X-ray CT apparatus according to claim 1, further comprising an input device configured to set the predetermined portion.

3. An X-ray CT apparatus according to claim 1, wherein the correlation data includes at least a correlation between a heartbeat rate and a static cardiac time phase.

4. An X-ray CT apparatus according to claim 1, further comprising
- memory means configured to store the projection data acquired over a plurality of heart beat cycles and
- a projection data synthesizing means configured to read the projection data corresponding to the static cardiac time phase detected by the detecting means and synthesizing the projection data,
- wherein the image reconstructing means reconstructs the projection data synthesized by the projection data synthesizing means.

5. An X-ray CT apparatus for generating a tomographic image by reconstructing projection data acquired by scanning a predetermined slice of a subject, said X-ray CT apparatus comprising
- detecting means configured to detect a static cardiac time phase with a small amount of motion artifacts in a predetermined portion in a heart, vicinity thereof or tissues moving along therewith, of the subject based on heartbeat information acquired in association with the projection data,
- image reconstructing means configured to generate the tomographic image by reconstructing projection data corresponding to the static cardiac time phase detected by the detecting means,
- sample tomographic image rearranging means configured to generate a plurality of sample tomographic images of respective different cardiac time phases based on the projection data and the heartbeat information, and
- selecting means configured to select a sample tomographic image with a small amount of motion artifacts from the plurality of sample tomographic images,
- wherein the detecting means determines the static cardiac time phase of the predetermined portion based on correlation data between the heartbeat information and the static cardiac time phase of each of a plurality of different portions of the subject, that are previously determined,
- wherein the image reconstructing means generates the tomographic image by reconstructing projection data corresponding to the cardiac time phase of the sample tomographic image selected by the selecting means, and
- wherein the selecting means calculates an integrated value of a CT value of each of the plurality of sample tomographic images in a predetermined region and selects a sample tomographic image with a smallest fluctuation of the integrated value of the CT value.

6. An X-ray CT apparatus according to claim 5, wherein an image size of the sample tomographic image is set smaller than that of the tomographic image.

7. An X-ray CT apparatus according to claim 5, further comprising
- memory means configured to store the projection data acquired over a plurality of heart beat cycles and
- projection data synthesizing means configured to read the projection data corresponding to the cardiac time phase of the sample tomographic image selected by the selecting means and synthesizing the projection data,
- wherein the image reconstructing means reconstructs the projection data synthesized by the projection data synthesizing means.

8. An X-ray CT apparatus according to claim 5, wherein the sample tomographic image generating means generates the plurality of sample tomographic images in a predetermined cardiac time phase range determined based on the correlation data between the heartbeat information and the static cardiac time phase that are determined previously.

9. An X-ray CT apparatus according to claim 8, wherein the correlation data is prepared to each of different portions of the subject, and the detecting means comprises input means for setting the predetermined portions.

10. An X-ray CT apparatus according to claim 8, wherein the correlation data includes at least a correlation between a heart rate and a static cardiac time phase.

11. An X-ray CT imaging method of generating a tomographic image by reconstructing projection data acquired by scanning a predetermined slice of a subject, said X-ray CT imaging method comprising
- (a) detecting a static cardiac time phase with a small amount of motion artifacts in a predetermined portion in a heart, vicinity thereof or tissues moving along therewith, of the subject based on heartbeat information acquired in association with the projection data, and
- (b) generating the tomographic image by reconstructing projection data corresponding to the detected static cardiac time phase,
- wherein said detecting the static cardiac time phase in (a) includes determining the static cardiac time phase of the predetermined portion based on correlation data between the heartbeat information and the static cardiac time phase of each of a plurality of different portions of the subject, that are previously determined.

12. An X-ray CT imaging method according to claim 11, further comprising acquiring the correlation data between the heartbeat information and the cardiac time phase from each subject, wherein the static cardiac time phase is detected based on the correlation data.

13. An X-ray CT imaging method according to claim 11, further comprising
- generating a plurality of sample tomographic images having respective different cardiac time phases based on the projection darn and the heartbeat information,
- selecting a sample tomographic image with a small amount of motion artifacts from the plurality or sample tomographic images, and
- using a cardiac time phase corresponding to the selected sample tomographic image as a static cardiac time phase.

14. An X-ray CT imaging method according to claim 13, wherein an image size of the sample tomographic image is set smaller than that of the tomographic image.

15. An X-ray CT imaging method according to claim 11, further comprising
- acquiring the correlation data between the heartbeat information and the static cardiac time phase from each subject, and
- generating the plurality of sample images in a predetermined cardiac time phase range determined based on the correlation data.

16. The X-ray CT imaging method of claim 11, further comprising:
- storing said correlation data in a memory, wherein the static cardiac time phase is determined based on the correlation data retrieved from said memory.

17. An X-ray CT apparatus according to claim 1, further comprising:
- memory means configured to store said correlation data,
- wherein the detecting means determines the static cardiac time phase of the predetermined portion based on the correlation data stored in said memory means.

18. An X-ray CT apparatus according to claim 1, wherein the correlation data stored in said memory means is obtained for each subject.

19. An X-ray CT apparatus according to claim 1, wherein the static cardiac time phase detected by the detecting means represents a tuning within a R wave cycle.

* * * * *